United States Patent [19]

Inoue

[11] 4,083,690
[45] Apr. 11, 1978

[54] AUTOMATIC PREPARATION OF SAMPLE FOR ANALYSIS

[75] Inventor: Takashi Inoue, Takasaki, Japan
[73] Assignee: Kirin Beer Kabushiki Kaisha, Japan
[21] Appl. No.: 727,109
[22] Filed: Sep. 27, 1976

[30] Foreign Application Priority Data

Oct. 2, 1975 Japan .................... 50-119074
Oct. 2, 1975 Japan .................... 50-135033

[51] Int. Cl.² .................... G01G 13/24; G01N 33/00; G01N 33/02
[52] U.S. Cl. .................... 23/230 M; 23/253 R; 23/259; 177/114; 426/231
[58] Field of Search ............ 23/230 M, 253 R, 259; 426/231; 177/114

[56] References Cited

U.S. PATENT DOCUMENTS

| | | | |
|---|---|---|---|
| 3,028,225 | 4/1962 | Sheen | 23/253 R |
| 3,236,321 | 2/1966 | Katagiri et al. | 177/114 |
| 3,515,672 | 6/1970 | Reinish et al. | 23/253 R X |
| 3,826,621 | 7/1974 | Johnson, Jr. et al. | 23/259 |
| 3,846,075 | 11/1974 | Cioffi | 23/253 R |
| 3,964,869 | 6/1976 | Aegidius | 23/253 R |

OTHER PUBLICATIONS

West et al., Studies on Diacetyl in Beer, American Society of Brewing Chemists, Proceedings, pp. 81-88 (1952).
Owades et al., Microdetermination of Diacetyl in Beer, American Society of Brewing Chemists, Proceedings, pp. 22-25 (1963).

Primary Examiner—Joseph Scovronek
Attorney, Agent, or Firm—Ladas, Parry, Von Gehr, Goldsmith & Deschamps

[57] ABSTRACT

A novel automatic apparatus for preparing a sample for analysis and a novel method for preparation of the sample are provided, whereby specified fractions of plural liquid samples can be automatically and successively collected by distillation. The apparatus comprises an inert gas charging means, a multi-way selector liquid sampler means operated by a timer, a liquid sample charging and discharging means operated by a timer, a distillation still, a fraction selector means and fraction receivers, which are connected in that order by pipe lines. The apparatus and method are especially useful, for example, for preparing a sample for analysis of a diacetyl-odor component and a sample for Kjeldahl determination method.

10 Claims, 10 Drawing Figures

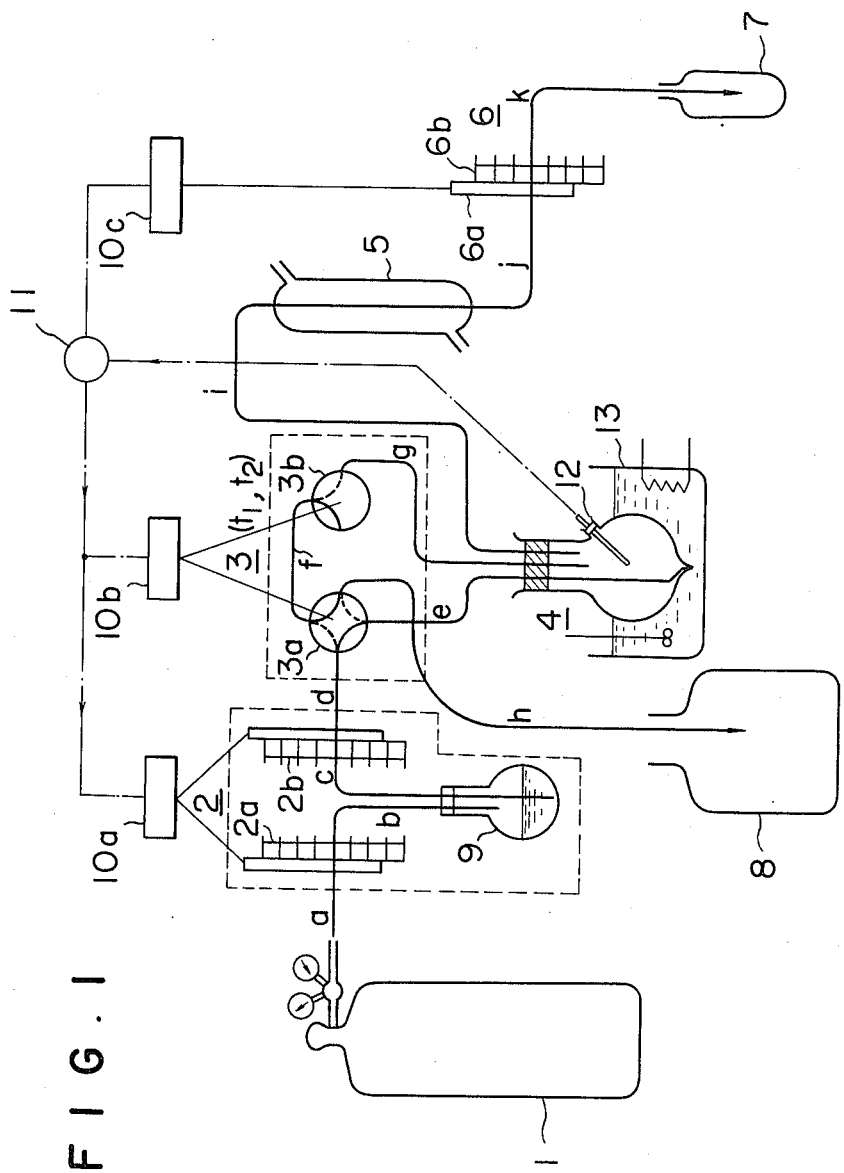
FIG. I

AUTOMATIC PREPARATION OF SAMPLE FOR ANALYSIS

BACKGROUND OF THE INVENTION (1) Field of the Invention

This invention relates to an apparatus and a method for automatically and successively collecting specified fractions contained in plural liquid samples by way of distillation (2) Description of the Prior Art Automatic analysis techniques have been remarkably developed in recent years. For instance, an apparatus which carries out without human hands an operation such as automatic addition of samples, automatic analysis, or automatic calculation of the resulting data is on the market. Such apparatus is applied for automatic colorimetry, automatic liquid or gas chromatography, and the like.

In a conventional apparatus for chromatography and the like, a sample for analysis is often prepared by removing an interfering substance from a starting sample by way of distillation. Such distillation operation for preparing a sample has been carried out by assembling a distillation apparatus for each starting sample. Such assembling of apparatus and control of distillation operation, however, are very troublesome when a large number of samples are handled for the purpose of a process control and the like. Moreover, such monotonous operations may give rise to aversion on the part of operators.

The present invention is concerned with a successive automation of distillation operation for preparing specified samples and has succeeded in reduction of labor.

SUMMARY OF THE INVENTION

An object of the present invention is to provide an apparatus for successive preparation of samples for analysis in which automatic operation is further promoted as far as the stage of preparation of a sample for analysis.

Another object of the present invention is to provide an automatic apparatus for preparing a sample for analysis, whereby specified fractions of plural liquid samples can be automatically and successively collected by way of distillation.

A further object of the present invention is to provide an automatic apparatus for preparing a sample for analysis of a diacetyl-odor component. An even further object of the present invention is to provide an automatic apparatus for successively preparing a sample for Kjeldahl determination method from a sample containing ammonia nitrogen.

A still further object of the present invention is to provide a method of preparing a sample for analysis by means of an apparatus of the present invention.

Other objects, features and advantages of the present invention will appear more fully from the following detailed description with reference to the accompanying drawings.

The apparatus of the present invention fundamentally comprises an inert gas charging means, a multi-way selector liquid sampler means operated by a timer, a liquid sample charging and discharging means operated by a timer, a distillation still, a fraction selector means, and fraction receivers, which are connected in that order by means of pipe lines, said liquid sample charging and discharging means including a multi-way changeover valve, said liquid sample charging and discharging means forming a passage extending from said multi-way selector liquid sampler means through the multi-way changeover valve to the bottom of said distillation still upon introduction of a liquid sample into said distillation still, said liquid sample charging and discharging means forming a passage connecting said multi-way selector liquid sampler means, said multi-way changeover valve, and space in said distillation still and a passage connecting the bottom of said distillation still, said multi-way changeover valve, and outside of the system upon discharging of a distillation liquid residue out of the system, The multi-way changeover valve comprises 4, 6 or more ways for connection. Modifications and variations of the apparatus can be made, for example, as described in the following detailed description

BRIEF DESCRIPTION OF THE DRAWINGS

In the drawings:

FIG. 1 is a flow diagram showing the essential organization of an example of an apparatus according to the present invention;

DETAILED DESCRIPTION

Figure 2A:
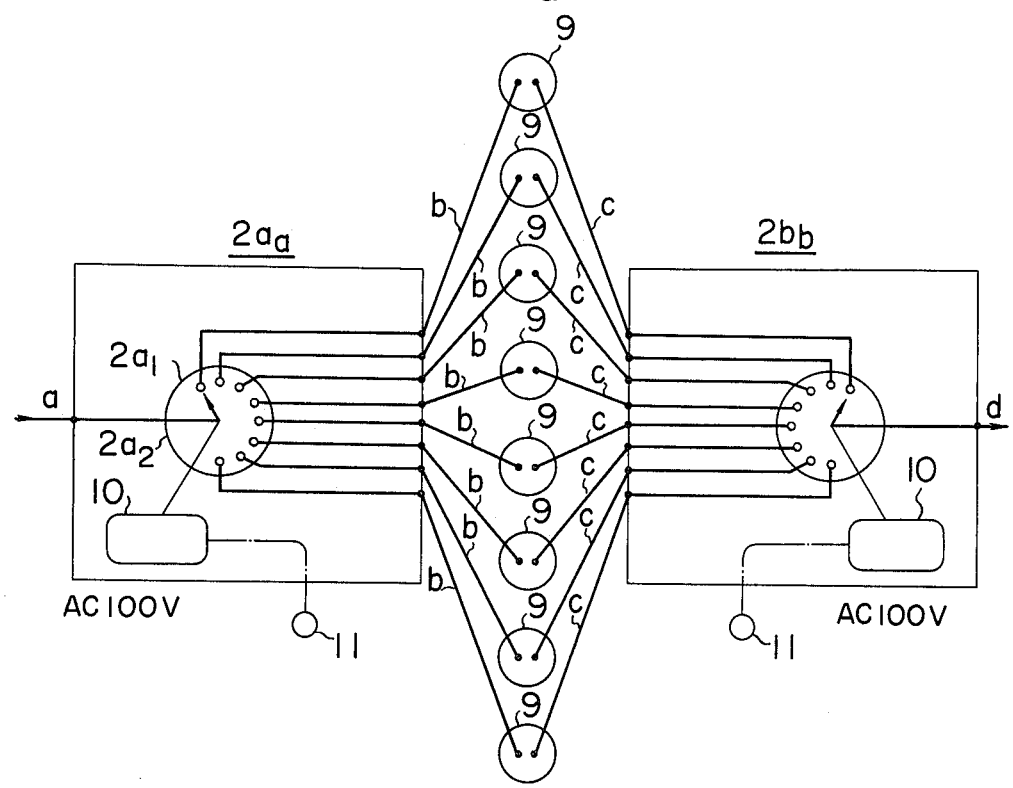
FIG. 2a is a diagrammatic view showing a multi-way selector liquid sampler means in which multi-way rotary selector valves are employed.

The invention is further explained by way of some preferred embodiments with reference to the drawings.

In the drawings, the heavy solid lines and dotted lines (showing flow passages in a changeover valve after switching over thereof) designate passages, the light solid lines driving means, the light dotted lines the apparatus blocks, and the dot-dash lines signal systems. Furthermore, the letters enclosed in parentheses following the reference numerals in the drawings stand for the points of time for operating the elements which are represented by the reference numerals in one cycle for preparation of a sample. For instance, the letters ($t_1$, $t_2$) appearing in the sample charging and discharging means 3 show that the passages are switched over from those represented by the solid lines to those of the dotted lines at $t_1$ in one cycle of the preparation process and are put back from those of the dotted lines to those of the solid lines at $t_2$ in one cycle. The letter ($t_1$) indicates that an element accompanied by $t_1$) is subjected to one switchover of the passage at a point of time $t_1$ in one cycle.

(1) A typical example of the present invention

A preferred example of the apparatus according to the present invention is illustrated in FIG. 1. This apparatus comprises: a cylinder 1 used as a gas charging means which is filled with a sample-carrying gas (a gas inert to a sample being generally employed and hereinafter referred to as carrier gas) under pressure; multi-way selector liquid sampler means 2 comprising a plurality of starting sample containers 9 (only one being shown in the drawing) which are connected to one pair of multi-way slide selector valves 2a and 2b by means of a plurality of sets of pipes b and c (only one set being shown); liquid sample charging and discharging means 3 comprising a four-way valve 3a, a two-way valve 3b, and a pipe f connecting the two valves; a distillation still 4; a condenser 5; a multi-way slide selector valve 6 to be used as a fraction selector means; and a plurality of fraction receivers 7 (only one being shown), which are connected in that order by means of pipes a, d, e and g, i, j and k (a plurality of pipes k being provided although one of them is shown).

The liquid sample charging and discharging means 3 is arranged to form a passage comprising pipe d . . . four-way valve 3a . . . pipe e extending to the bottom of the distillation still 4 upon charging a liquid sample into the distillation still 4, and to form both a passage comprising pipe d . . . four-way valve 3a . . . two-way valve 3b . . . pipe g extending to the inside space of the distillation still and a passage comprising pipe e extending to the bottom of the distillation still . . . four-way valve 3a . . . a distillation liquid residue-waste bottle 8 outside of the system upon discharging a distillation liquid residue from the distillation still 4.

Further, the multi-way selector valves 2a and 2b, the four-way valve 3a, and the two-way valve 3b as well as the multi-way selector valve 6 are driven by motors 10a, 10b and 10c, respectively, these motors being operated by a timer 11 receiving a starting input from a thermometer 12 provided in the distillation still 4. The distillation still is heated, for example, in a heating bath 13 provided with stirring blades and a heater. The multi-way slide selector valves 2a, 2b and 6 are essentially of the same construction. For example, the multi-way selector valve 6 comprises a movable plate 6a having a passage connected to a flexible pipe j and a fixed plate 6b having passages connected to a plurality of fixed pipes k, and is adapted to select one passage from those in the fixed plate, the movable plate 6a being moved by means of the motor 10c.

The operation of the apparatus described above and shown in FIG. 1 is as follows. An inert gas which has been reduced to a suitable pressure is introduced into the upper space of a starting sample container 9 from the cylinder 1 through one passage of the multi-way selector valve 2a and a pipe b, and a starting liquid sample in the container 9 is charged into the distillation still 4 by gas pressure through the pipe c extending to the bottom of the container 9 . . . one passage of the multi-way slide selector valve 2b . . . the pipe d . . . the four-way valve 3a (the passage shown by solid line in the drawing) . . . the pipe e extending to the bottom of the distillation still 4. The starting liquid sample thus charged is indirectly heated in the heating bath 13, whereby a specified fraction is distilled off from the distillation still 4 and cooled by means of the condenser 5, and then stored in one of the fraction receivers 7 through one passage of the multi-way slide selector valve 6 and one of the pipes k connected thereto. Thus, a sample of analysis which is used in a subsequent analysis process is obtained.

When distillation of the specified fraction from the distillation still 4 has been completed, the temperature detected by the thermometer 12 is elevated in accordance with distillation of a higher boiling-point fraction. The timer 11 is allowed to start at this point of time ($t_1$). At the same time, the selector valve 6 is switched over to the next passage, and the changeover valves 3a and 3b are also switched to the passages shown by the dotted lines in the drawing. As a consequence, the inert gas flows from the empty starting sample container 9 into the interior space of the distillation still 4 through the pipes d, f, and g. Distillation liquid residue in the distillation still 4 is discharged into the liquid residue waste bottle 8 through pipes e and h by the gas pressure. This discharging operation will generally be terminated in 1 to 2 minutes. Then, the passages of the changeover valves 3a and 3b are returned to the positions shown by the solid lines in connection with the signal of the timer which was set at a point of time $t_2 (= t_1 + 1 - 2$ minutes). The slide selector valves 2a and 2b are also switched by means of the motor 10a to the next passage connected to another starting sample container 9 (not shown in the drawing) through other pipes b and c (not shown). Further, the slide selector valve 6 is driven by the motor 10c to select the next fraction receiver 7 (not shown in the drawing).

In the above described operations, starting point of the timer can also be set to a point of time for switching over the slide selector valves 2a and 2b, or a point of time when the temperature of vapor detected by the thermometer 12 which was once cooled by charging a starting sample is raised near to the distillation temperature of a specified fraction, which may be referred to as a point of time "0". In this case, the operations at the points of time $t_1$ and $t_2$ are the same as those mentioned above. The period of time for charging a sample and carrying out distillation (a period of time of $t_1$ in this case) is approximately a constant time when the starting liquid sample is supplied in approximately same quantity and the heating velocity of the heating bath 13 is constant. Thus, such change in the starting point becomes possible.

Figure 2B:
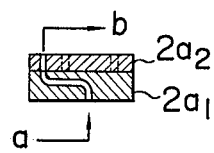
FIG. 2b is a vertical section of a rotary selector valve.
Figure 2C:
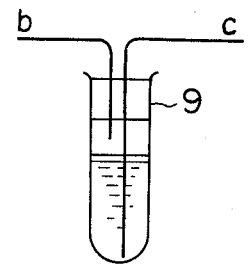
FIG. 2c is a diagrammatic elevation of a starting sample container.

The example shown in FIG. 1 can be modified or changed in various ways. For instance, the cylinder 1 can be replaced by a gas-metering pump. The multi-way selector liquid sampler means 2 may comprise a pair of multi-way rotary selector valves 2aa and 2bb as shown in FIG. 2a. FIG. 2b is an elevational view in section of rotary selection members of the selector valve 2aa. The rotary selector valve comprises a rotary disk $2a_1$ and a fixed disk $2a_2$. The lower introduction part of the rotary disk located on the center line of the disks is sealed and rotatably connected to the pipe a. Thus the pipes a and b need not be flexible. FIG. 2c is an elevational view of a starting sample receiver 9 of which a top plan view appears in FIG. 2a.

Figure 3:
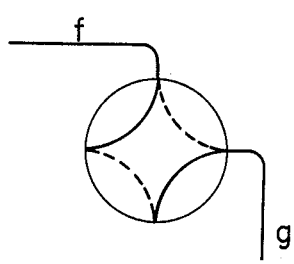
FIG. 3 is a diagrammatic view showing the flow passages of a four-way changeover valve (hereinafter sometimes referred to as "four-way valve") which can be substituted for a two-way changeover valve (hereinafter sometimes referred to as "two-way valve") in the liquid sample charging and discharging means shown in FIG. 1.
Figure 8:
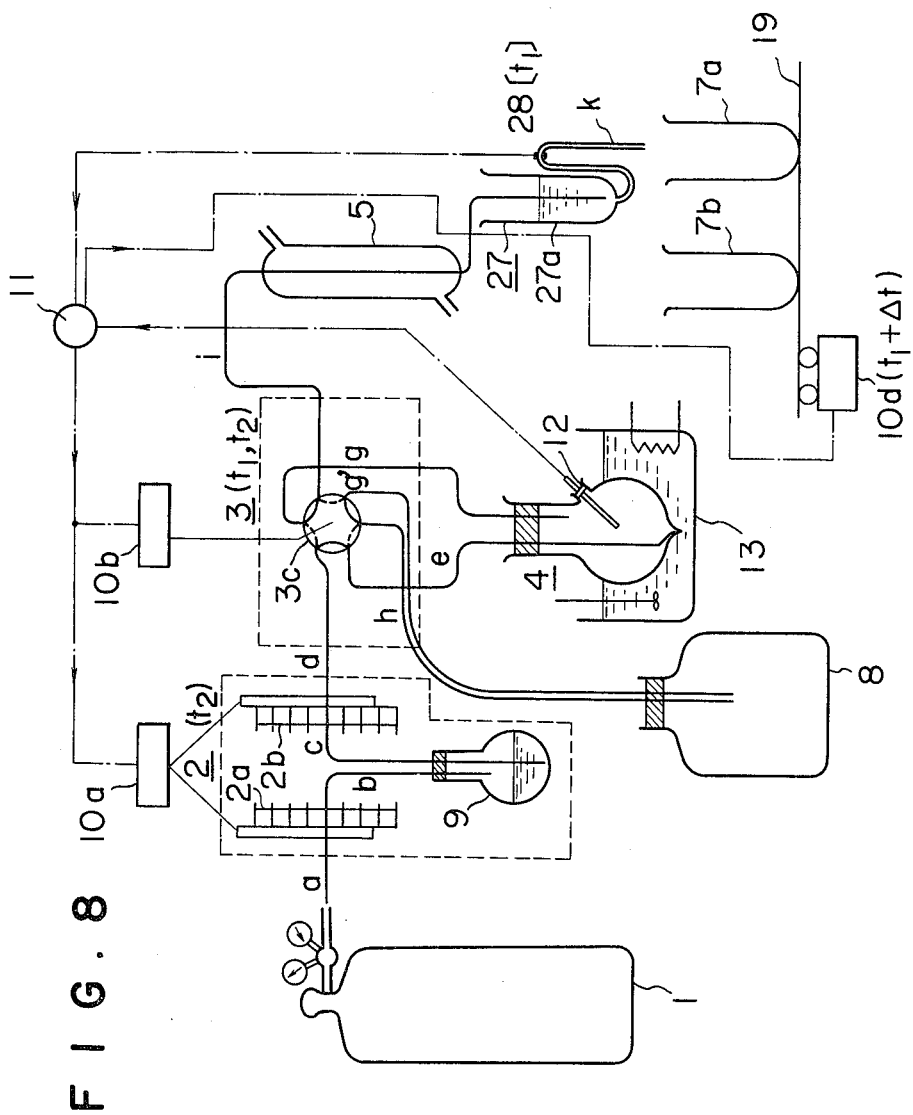
FIG. 8 is a flow diagram showing a modification of the example shown in FIG. 1, wherein a liquid sample charging and discharging means comprising a six-way valve, and a siphon-type fraction collector are used.

The two-way valve shown in FIG. 1 may be a four-way valve as shown by FIG. 3 (in the drawing a passage end represented by a black dot indicates a plugged state), or may simply be an electromagnetic valve which is intercoupled with the timer 11 so as to open for only the time period of $t_1$ to $t_2$ mentioned above, or may further be integrated with the four-way valve to form a six-way valve 3c disposed as shown in FIG. 8. In the last case, as shown in FIG. 8, the liquid sample charging and discharging means is composed solely of the six-way valve 3c; and is arranged to form a passage comprising pipe d . . . six-way valve 3c . . . pipe e extending to the bottom of the distillation still 4 upon charging a liquid sample into the distillation still 4 (shown by solid lines in the six-way valve 3c), and to form both a passage comprising pipe d . . . six-way valve 3c . . . pipe g extending to the inside space of the distillation still and a passage comprising pipe e extending to the bottom of the distillation still . . . six-way valve 3c . . . pipe h . . . a distillation liquid residue waste bottle 8 outside of the system upon discharging a distillation liquid residue from the distillation still (shown by dotted lines in the six-way valve 3c).

Figure 4:
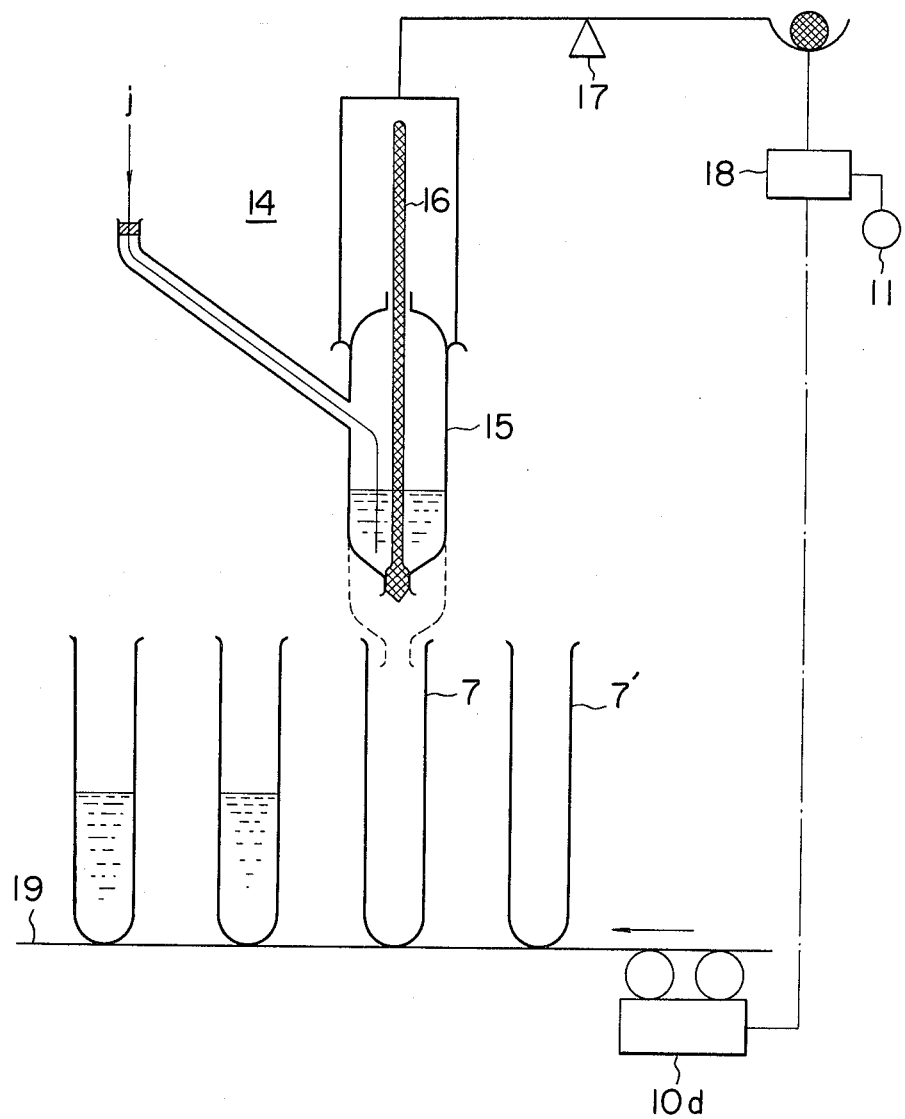
FIG. 4 is a flow diagram showing a fraction collector which can be substituted for the multi-way slide selector valve shown in FIG. 1.

Furthermore, the multi-way slide selector valve 6 can be replaced by a gravimetric fraction collector 14 as shown in FIG. 4 (the body comprising a movable receiver 15 and a fixed stopper 16). In this case, the pipe k is omitted. The operation of the fraction collector is as follows. When a predetermined amount of liquid distillate has been stored in the movable receiver 15 through the pipe j, the receiver 15 descends by gravity as low as the position shown by the dotted line. At this time, a microswitch 18 which is mechanically connected to the receiver 15 via a fulcrum 17 is turned on, and a starting signal (a point of time $t_1$) is sent to the timer 11, and the passages of the valves 2a, 2b, 3a and 3b are switched over. The liquid in the receiver 15 flows down into the fraction receiver 9 since the stopper 16 is fixed. When the movable receiver 15 becomes empty and returns to the original position, the driving motor 10d is operated to move a stand 19 until the succeeding fraction receiver 7 comes under the movable receiver 15 in accordance with either a signal sent by the microswitch 18 which is switched off or a signal at a point of time $t_1 + \Delta t$ sent by the timer 11 ($\Delta t$ is adjusted to be slightly longer than the time in which the receiver 15 becomes empty).

The started timer causes passages to switch over at a time $t_2$ (= "0") thereby to start collection of the succeeding sample in the same way as described above with reference to FIG. 1. Furthermore, the ascent and descent of the movable receiver can also be accomplished by a timer signal of the timer with the starting point ($t_1$ or "0") determined by a signal from the thermometer 12 in the distillation still as shown in FIG. 1 or by the switchover signal from the multi-way slide selector valves 2a and 2b. As described above, by employing a fraction collector and especially by starting the timer when the movable receiver descends, it becomes possible to decrease the time lag between the cycle of the timer and the actual cycle of distillation and to ensure collection of a predetermined volume of a fractionated sample.

Instead of the gravimetric fraction collector 14, a siphon-type fraction collector 27 as shown in FIG. 8 may be used as a fraction selector means. The siphon-type fraction collector 27 comprises a container 27a having a siphon-pipe k connected to the bottom thereof. When a predetermined amount, corresponding to the height of the top point of the siphon-pipe k, of a liquid distillate is stored in the container, the liquid distillate starts to overflow the siphon-pipe and run out of the container into the receiver 19 to empty the container due to the siphon effect. The siphon-type fraction collector can be provided with e.g. a means 28 for detecting the overflow of the liquid distillate through the siphon-pipe k which can send a starting signal (a point of time $t_1$) to the timer 11. The switching-over of the valves 2a, 2b and 3c and the transfer of the receivers 7 by motor 10d are effected by time signal from the timer 11 as explained in respect of gravimetric fraction collector 14.

Figure 5:
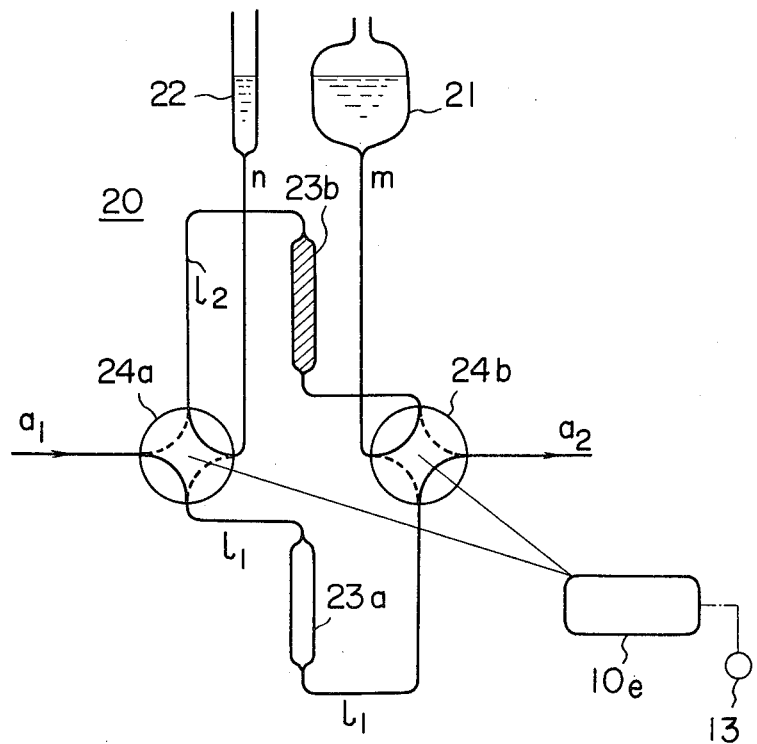
FIG. 5 is a flow diagram showing reagent addition means which can be interposed in the piping of the apparatus shown in FIG. 1.

In the example shown in FIG. 1, a reagent addition means 20 as shown in FIG. 5 can further be interposed in the pipe line a, d, j, or the like. The reagents to be added include a reaction reagent for a reactive distillation, a thermal stabilizer for a distillation, a liquid distillate conditioner for preparing a sample for the subsequent analysis process, a fraction collector agent and the like, and are added in a solution state. FIG. 5 illustrates a reagent addition means 20 which is, for example, to be interposed in the pipe line as shown in FIG. 1. The means 20 comprises a reagent container 21, an overflow-preventing pipe 22, metering tubes 23a and 23b, a pair of four-way valves 24a and 24b, and pipes $l_1$, $l_2$, m and n connecting these components.

The reagent introduced into the pipe $l_1$ and the metering tube 23a is driven out by a carrier gas from the pipe $a_1$ and sent to the multi-way selector liquid sampler means 2 through the pipe $a_2$. While the reagent is added through the pipe $l_1$ and the tube 23a, the reagent solution flows down by gravity from the reagent container through the pipe m and is introduced into the pipe $l_2$ and the metering tube 23b. At the starting point ($t_2$ = "0") of the subsequent analysis cycle, the four-way valves 24a and 24b are switched over to the passages shown by the dotted lines, and the reagent in the pipe $l_2$ and the tube 23b is driven out by a carrier gas and sent to the sampler means 2. In FIG. 5, a feed pump may be placed in the pipe m. In this case, a cyclic system of the reagent solution is formed by connecting the upper ends of the bottle 21 and the pipe 22 with a pipe.

Some illustrative and interesting applications within the scope of the present invention will now be described.

(2) An apparatus for preparing a sample for analysis which is used for a quantitative analysis of a diacetyl odor component contained in an aqueous solution.

A diacetyl-odor component (generally containing 2,3-pentanedione in addition to diacetyl) produced in a fermented food plays an important role as a flavor component in the fermented food. In the case of beer, however, a diacetyl-odor component gives it an unpleasant smell even when only a minute amount thereof is present in beer, and it is desirable therefore to minimize the component. Accordingly, not only the research on a production process in which formation of a diacetyl-odor component is prevented but also development of a method for rapidly and accurately determining a diacetyl-odor component have been desired from the standpoint of process control. According to one aspect of the present invention, there is provided a method for automatic and successive preparation of a concentrated aqueous diacetyl-odor component solution which is necessary for determination of a diacetyl-odor component contained in such food, especially aqueous food and drink such as beer, as well as an apparatus for carrying out the method for preparation.

The microcolorimetric method by Owades and Jakovac (Proc. Am.Soc. Brewing Chemists pages 22–25, (1963)), hereinafter referred to as Owades method, has been widely applied to the quantitative analysis of a diacetyl-odor component in such food since the method is advantages in that only a small quantity of a sample is required and multiple samples (maximum 12 samples) can be simultaneously treated. However, upon application of this method to a beer sample, the method is not entirely satisfactory in that a gas-washing operation which is required for condensing the diacetyl-odor component takes 2 hours, and it is troublesome to assemble the apparatus everytime the analysis is conducted.

The present inventor has studied the Owades method and found that this deficiency of this method is due to the fact that the gas-washing operation is carried out at a low temperature in order to completely collect or trap the diacetyl-odor component and to suppress evaporation of water. The present inventor, however, has further found that loss of the diacetyl-odor component is not observed even when the washing is carried out at a temperature between the boiling point of diacetyl and that of water by collecting the gas which comes out from the washer and is cooled, and a sample for analysis of the diacetyl-odor component is obtained in a concentration which is required for colorimetry, and that the time necessary for the gas-washing operation can thus be shortened to 30 minutes or less for one sample.

On the basis of these findings, the present inventor has continued his study and has found further that the diacetyl-odor component can be automatically and successively condensed and collected from a plurality of samples by employing an inert gas which is suitable as the washing gas, as a carrier gas for charging a sample to a gas washer and discharging a liquid residue from the gas washer out of the system, and as a carrier gas of a collector agent to a collector. The apparatus of the present invention is especially suitable for carrying out this method.

Figure 6:
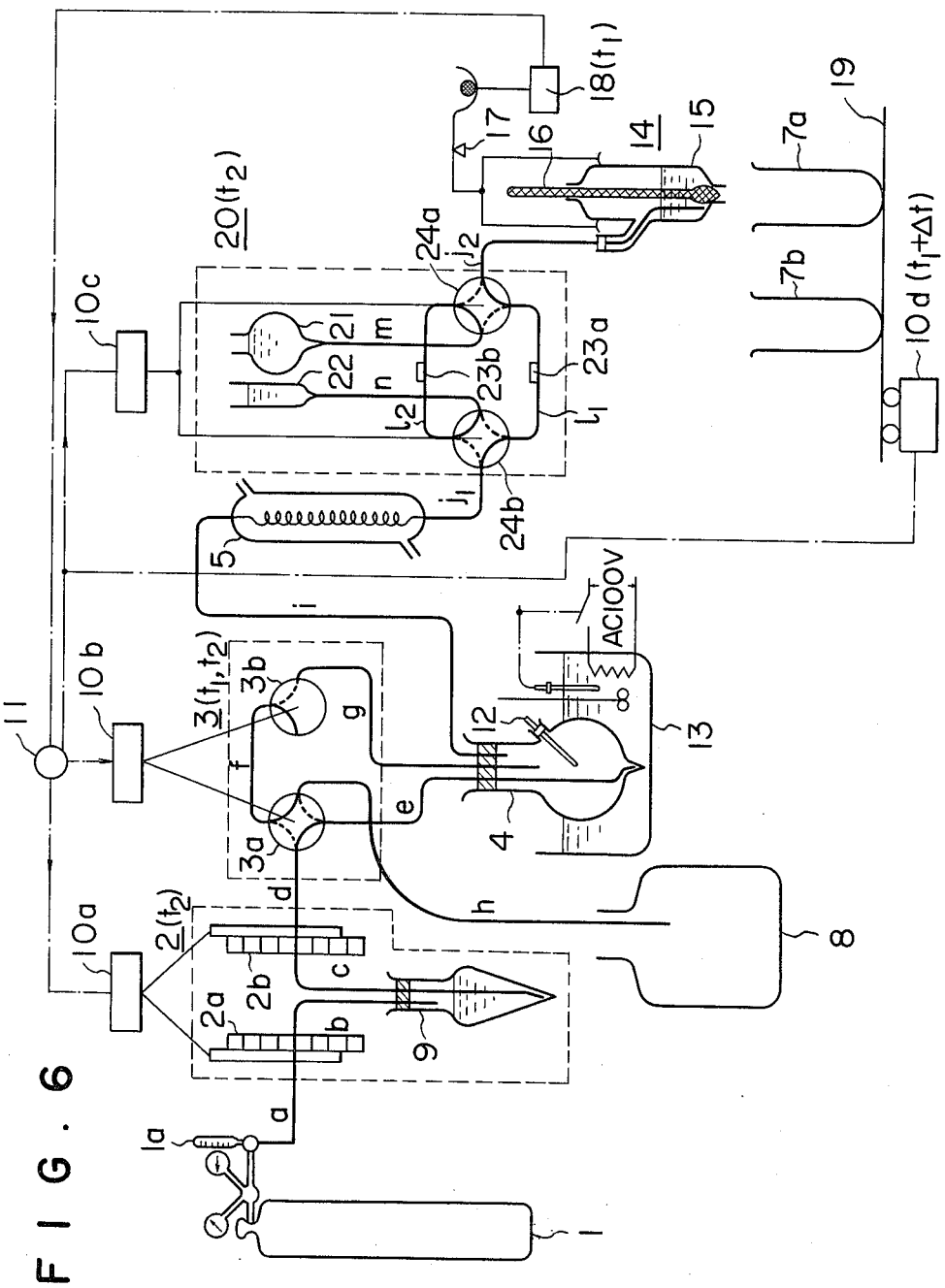
FIGS. 6 and 7 are flow diagrams showing other examples of the present invention.

As an example of the present invention, an apparatus for preparing a sample for analysis of a diaceyl-odor component is illustrated in FIG. 6. As shown in FIG. 6, there are connected by means of pipes: a cylinder 1, as an inert gas charging means, provided with a flow meter 1a and filled with an inert gas; a multi-way selector liquid sampler means 2 comprising a pair of multi-way slide valves 2a and 2b and a plurality of starting sample containers 9 (only one being shown in the drawing) which are connected to the valves with plural pairs of pipes b and c (only one pair being shown); a liquid sample charging and discharging means 3 comprising a four-way valve 3a, a two-way valve 3b and a pipe $f$ connecting them; a gas washer 4 provided with a thermometer 12 and immersed in a thermostatic heating bath 13; a condenser 5; a diacetyl-collector agent addition means 20 comprising a diacetyl-collector agent container 21, a pair of four-way valves 24a and 24b and an overflow-preventing pipe 22, which are connected by a pipe $m$ a pipe $l_1$ having a metering tube 23a, a pipe $l_2$ having a metering tube 23b and a pipe $n$; a gravimetric fraction collector 14 used as a fraction selector means comprising a movable receiver 15 mechanically connected to a microswitch 18 via fulcrum 17 and a fixed stopper 16 which is fitted to the bottom of the receiver by way of a ground glass fitting; and a fraction receiver 7a placed under the receiver 15, respectively in this order. In this connection, a pipe between the fraction collector 14 and the fraction receiver 7a may be omitted as in this example.

The liquid sample charging and discharging means 3 including the four-way valve 3a is arranged to form a path comprising the multi-way selector liquid sampler means 2 ... the pipe $d$ ... the four-way valve 3a ... the pipe $e$ extending to the bottom of the gas washer 4, when the liquid sample is charged to the gas washer 4 and is then washed in the washer by the inert gas and to form both a path connecting the pipe $d$ ... the four-way valve 3a ... the pipe $f$ ... the two-way valve 3b ... the pipe $g$ extending to the inside space of the gas washer and a path connecting the pipe $e$ extending from the bottom of the gas washer ... the four-way valve ... a liquid waste bottle 8 outside of the system when the gas-washed liquid residue is discharged from the gas washer. Moreover, each pair of the multi-way slide selector valves 2a and 2b, the four-way valves 3a and 3b, and the four-way valves 24a and 24b ar driven to switch over the passages by means of driving motors 10a, 10b and 10c, respectively, these motors and a motor 10d for moving a stand 19 of the fraction receivers 7a, 7b ... being arranged to be driven in response to a signal from a timer 11 which is started by the input from the microswitch.

The method of preparing a sample for analysis of a diacetyl-odor component by means of the apparatus shown in FIG. 6 will now be described. An inert gas which is used as a washing gas and a carrier gas is not particularly limited as long as it is inert with respect to a starting sample containing diacetyl. Carbon dioxide, nitrogen and air are generally employed and, of these, carbon dioxide is especially employed. Carbon dioxide is used as the inert gas in the following embodiment of the invention. The starting sample is an aqueous solution containing a diacetyl-odor component and is typically a sample of a beer. In this case, the starting sample contains about 0.04 – 2 ppm of a diacetyl-odor component as well as 0 to 6% of alcohol, various extracts from raw materials such as malt and various fermentation products. Presence of up to 10% of alcohol and other impurities in the starting sample does not interfere with preparation of sample according to the present invention and a subsequent analysis. A plurality of starting samples are charged into respective starting sample containers 9 (only one of which is shown in the drawing) in a predetermined amount respectively. Before the start of the operation, the containers 9 have been connected to one passage of the multi-way selector valves 2a and 2b by the pipes b and c, respectively. At a point of time for starting operation (a point of time "0"), the passages shown by the solid lines in the drawing have been formed.

Carbon dioxide from the cylinder 1 is reduced to a suitable pressure and its flow is controlled by means of the flow meter 1a. Then the carbon dioxide is continuously introduced into the upper space of the starting material container 9 through one passage of the multi-way slide selector valve 2a and the pipe b. By the carbon dioxide pressure, a starting sample is charged into the bottom of the gas washer 4 through the pipe c inserted into the bottom of the container 9 ... one passage of the multi-way selector valve 2b ... the pipe $d$ ... the four-way valve 3a ... the pipe $e$. Carbon dioxide is further introduced into the gas washer as a washing gas after having charged the starting sample. The gas washer 4 is immersed in a heating bath 10 which is controlled at a temperature not lower than the boiling point of diacetyl and below the boiling point of water, that is, at about 88° to 100° C. Accordingly, the starting sample charged in the gas washer is maintained in the course of washing at a temperature of approximately the same as or a little lower than the temperature of the heating bath.

By washing the sample with gas, carbon dioxide accompanied by a diacetyl-odor component, moisture, etc., is introduced into the collector agent addition means 20 through the pipe $i$ and condenser 5, diacetyl, alcohol, water, and other various volatile components being condensed at the condenser 5. The carbon dioxide carries, in its initial stage of flow, a collector agent in the metering tube 23a in the means 20 into the movable receiver 15 in the fraction collector 14 through the pipe $j_2$. Then the carbon dioxide flows upwards in the collector agent from the pipe $j_2$ inserted in the bottom of the receiver 15 and is released outside the system from the upper end of the receiver 15, and the diacetyl-odor component is removed when the gas is passing upward through the collector agent.

During the washing with carbon dioxide, a predetermined amount of the collector agent flowing down from the collector agent container 21 in the collector agent addition means 20 enters the metering tube 23b by gravity for the next collection cycle. As the collector agent, an aqueous solution of hydroxylamine hydrochloride, an aqueous solution of the salt thereof neutralized with sodium acetate, or the like is generally employed. The diacetyl-odor component thus collected is converted to diacetyl dioxime during the collecting operation and/or by heating the component thereafter, which is used as a sample for a subsequent colorimetry.

The washing with gas is continued for a little while after the diacetyl-odor component has been distilled off completely from the gas washer 4. In the meantime, distilled water is collected in the movable receiver 15 of the fraction collector. When the liquid in the receiver 15 reaches a predetermined quantity (this quantity having been determined experimentally by the quantity of liquid which has been collected during the time necessary to distill off the diacetyl-odor component), the movable receiver 15 descends and a liquid distillate containing a diacetyl-odor component (sample for analysis) is collected in the fraction receiver 7a since the fixed stopper 16 does not move. At the same time, the microswitch 18 connected to the receiver 15 via the fulcrum 17 is switched on, a starting signal (at a point of time $t_1$) thereby being sent to the timer 11, and the passages of the changeover valves 3a and 3b are switched over to those represented by the dotted lines. When the receiver becomes empty and returns to the upper position, the microswitch 18 is switched off. In accordance with the signal sent from the microswitch or the signal at a point of time $t_1 + \Delta t$ sent from the timer ($\Delta t$ being set to be a little longer than the time during which the receiver 15 becomes empty), the driving motor operates to move the next fraction receiver 7b on the stand 19 under the movable receiver 15.

On the other hand, as a result of the switching at a point of time $t_1$ of the changeover valves 3a and 3b to the passages represented by the dotted lines in the drawing, the washing with gas is terminated, and the liquid residue in the gas washer 4 is discharged outside the system by the carbon dioxide which flows continuously. More specifically, carbon dioxide is introduced into the upper space of the gas washer 4 through the pipe $d$ . . . the four-way valve 7a . . . the pipe $f$ . . . the two-way valve 7b, and the washed liquid residue is discharged into the waste bottle 8 from the bottom of the washer 4 through the pipe $e$ . . . the four-way valve 3a . . . the pipe $h$ by the gas pressure. At this time, a signal at the time $t_2$ is sent from the timer, whereby the changeover valves 3a and 3b are switched over to the passages represented by the solid lines, and the multiway selector valves 2a and 2b are switched over to the succeeding passage. Further, the changeover valves 24a and 24b are changed to the passages represented by the dotted lines. The suceeding cycle for preparation of sample is thus started. Successive preparation of sample for analysis can be performed by repeating the preparation cycle.

In the above described operation, there is a considerable diversity in the cycle of the timer. For example, in the case where the timer system is set to a point of time "0" when the cycle of preparation of sample is started, a point of time $t_1$ when washing is terminated (that is, when discharge of liquid residue is started), and a point of time $t_2$ when discharge of liquid residue is terminated (that is, when the succeeding cycle of sample preparation is started), the following modifications can be made. Of course, other modifications can be made by setting the timer in other ways.

(a) The starting point of the timer is set to a point of time $t_2$ when the motor 10d is driven.

(b) The starting point of the timer is set to a point of time $t_1$ when the movable receiver 15 returns to the upper position to turn on the microswitch 18.

(c) The starting point of the timer is set to a point of time "0" when washing with gas is started. That is, switchover of all the passages including ascending and descending of the movable receiver 15 is carried out in accordance with the signals from the timer by setting the starting point "0" of the timer to a point of time when the temperature in the gas washer 4 is lowered owing to the introduction of a starting sample thereinto or the temperature is then elevated to a predetermined temperature.

(d) The starting point of the timer (a point of time "0") is set to the time when the passages of the multiway slide valves 2a and 2b are switched over.

The apparatus illustrated in FIG. 6 can also assume various modified forms similarly as described with respect to the apparatus shown in FIG. 1. For example, the cylinder 1 with the flow meter 1a can be replaced by a gas-metering pump. The multi-way selector liquid sampler means 2 may comprise a pair of multi-way rotary selector valves $2_{aa}$ and $2_{bb}$ as shown in FIG. 2a.

Furthermore, the two-way changeover valve in the liquid charging and discharging means 3 as shown in FIG. 6 may be the four-way changeover valve as shown in FIG. 3 (the passage end represented by a black dot indicates a tightly stoppered state in the drawing), or an electromagnetic valve which is intercoupled with the timer so as to open for a time period of the above-mentioned time $t_1$ to $t_2$.

Moreover, the combination of the fraction collector 14 with the fraction receiver 7 may be replaced by that of the multi-way slide selector valve 6 with the fraction receiver 7 as shown in FIG. 1. In this case, the fraction receiver 7 operates also as a diacetyl-odor component collector means, and, accordingly, it is necessary to extend the pipe $k$ to the bottom of the receiver 7.

Samples for analysis of a diacetyl-odor component were prepared by using the apparatus shown in FIG. 6 in which the multi-way selector liquid sampler means 2 was replaced by the one including the multi-way rotary selector valve shown in FIG. 2. The results were as follows.

Before starting the process for preparation of samples, 8 starting samples (samples of beer) each of 40 ml were connected to respective passages of the multi-way selector liquid sampler means 2. These 8 starting samples contained 0.2, 0.2, 0.5, 0.5, 1.0, 1.0, 2.0, and 2.0 ppm of diacetyl-odor components, respectively. The samples for analysis were prepared and collected in 8 fraction receivers by passing carbon dioxide at a rate of 175 ml per minute under the conditions of a washing time with the gas ("0" → $t_1$) of approximately 28 minutes, time for discharging washed liquid residue ($t_1$ → $t_2$) of approximately 2 minutes, one cycle of approximately 30 minutes, and a total time required of approximately 240 minutes. These samples for analysis were subjected to colorimetry according to the Prill-Hammer method, the results of which are shown in the following Table 1.

In the preparation process, 0.6 ml (per sample) of 4.4% aqueous solution of hydroxylamine hydrochloride was employed as a collector agent. The starting point of the timer was set to a point of time ($t_1$) when 4 ml of the sample was collected in the movable receiver 15 of the fraction collector and the receiver 15 descended. The thermostatic bath 10 was maintained at 90° C.

The results of analysis which were obtained by carrying out the operation strictly according to the Owades method (starting sample 30 ml) are also shown in Table 1 for comparison. In this case, the period of time required for washing with gas for preparing the sample for the colorimetry was about 2 hours per sample.

Table 1

| Sample | Concentration of diacetyl (ppm) | |
|---|---|---|
| | Owades method (manual) | Method of this invention |
| 1 | 0.19 | 0.21 |
| 2 | 0.18 | 0.20 |
| 3 | 0.48 | 0.47 |
| 4 | 0.47 | 0.49 |
| 5 | 0.97 | 0.98 |
| 6 | 0.98 | 1.03 |
| 7 | 1.99 | 1.95 |
| 8 | 2.03 | 2.01 |

As clearly shown from the data in Table 1, no substantial difference in analytical accuracy can be observed between the samples obtained by the present invention and those by the Owades method. Thus, it can be appreciated that the present invention greatly contributes to the shortening of washing operation time and automation of the analytical process.

(3) An automatic and successive apparatus for the process of steam distillation of ammonia nitrogen in the Kjeldahl nitrogen determination method.

Figure 7:
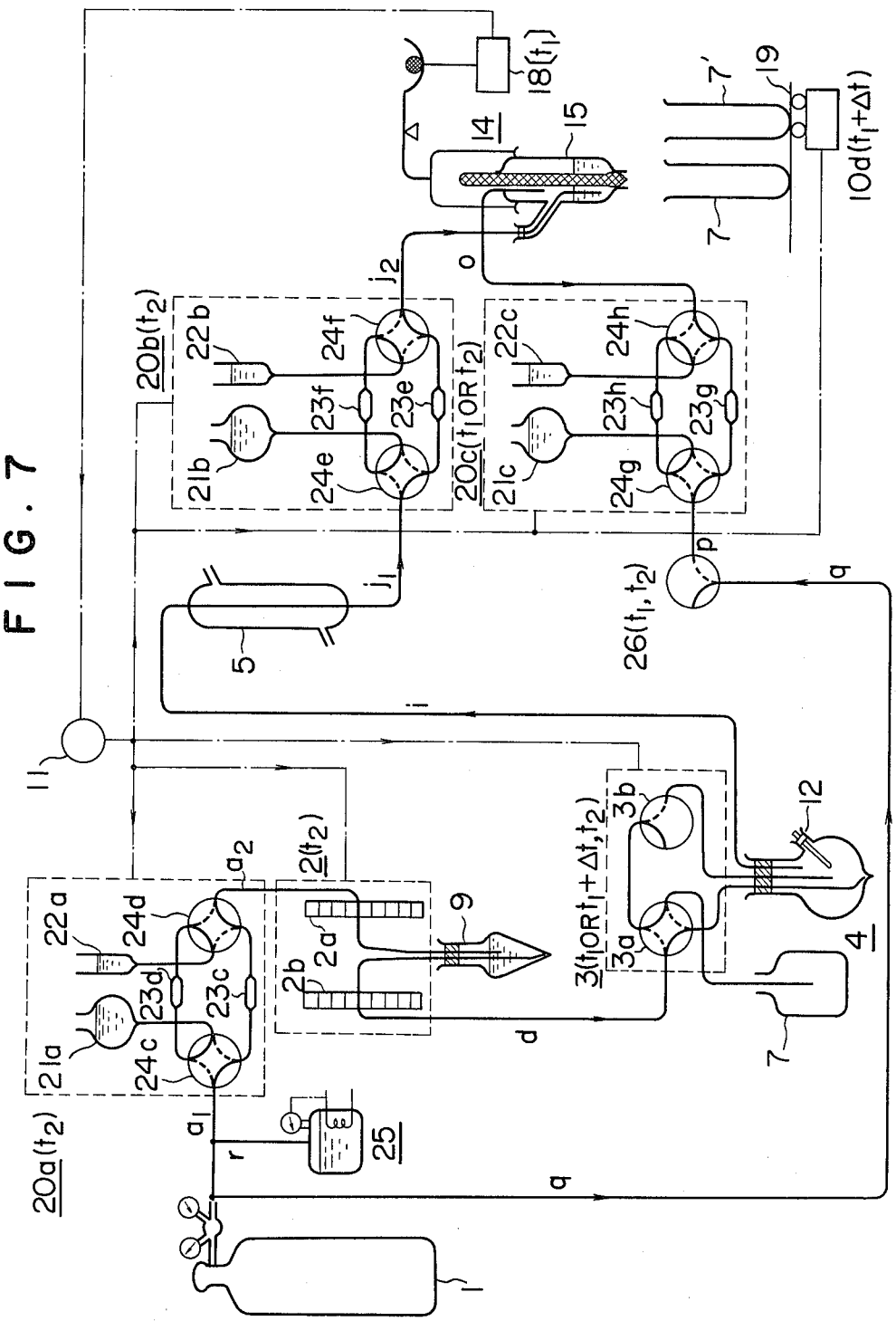

Another significant embodiment of the present invention is the above-mentioned apparatus. The process of the Kjeldahl determination method comprises the three stages of decomposition of nitrogen-containing compounds contained in a sample into ammonia, steam distillation of ammonia nitrogen, and determination by titration. Of these three stages, the first decomposition process takes a considerably long time but requires almost no human operation; the last titration process can be carried out in a short period of time manually or by means of an automatic titration apparatus; but the steam distillation process requires human operation and some time and is accompanied by some danger such as that due to handling of a concentrated alkali. In accordance with the present invention, the steam distillation process can be advantageously automated to reduce labor and utilize idle time and to remove the dangers due to the operation. The apparatus for this process is illustrated in FIG. 7.

The apparatus shown in FIG. 7 can be described with reference to FIG. 1 as a modification of the apparatus shown in FIG. 1, differing therefrom in the following features. A steam generator 25 (via a branch pipe r) and an aqueous sodium hydroxide solution addition means 20a are installed in a pipe line a, and an aqueous sulfuric acid solution addition means 20b is installed in a pipe line j, respectively, in the apparatus shown in FIG. 1. A gravi-metric fraction collector 14 as shown in FIG. 4 is employed instead of the multi-way slide selector valve 6, and a washing water addition means 20c is connected to the fraction collector via a pipe o, the addition means 20c being connected to an outlet pipe $a_1$ of a cylinder 1 by means of pipes p and q including a two-way valve 26. The addition means 20a, 20b and 20c are essentially identical to the reagent addition means shown in FIG. 5 in both structure and operation, and differ only in the species of reagent and the location. Illustration of a heating bath of the distillation still and driving motors of the changeover valves is omitted in FIG. 7.

The operation of the apparatus shown in FIG. 7, briefly described, is as follows. The passages shown by the solid lines in the drawing are formed at a time "0" (which corresponds to a time $t_2$ mentioned below). A carrier gas from the cylinder 1 accompanied by steam from the steam generator 25 through the pipe $a_1$ drives out a predetermined quantity of an aqueous sodium hydroxide solution at the sodium hydroxide addition means 20a, and further drives out a predetermined quantity of a sample containing decomposed ammonia through one passage of the multi-way selector liquid sampler means 2 thereby to charge the distillation still 4. In the distillation still 4 steam distillation of ammonia nitrogen is started. Distilled vapor is condensed through a condenser 5 and is introduced into the movable receiver 15 of the fraction collector 14 together with a predetermined quantity of sulfuric acid from the sulfuric acid addition means 20b. Sulfuric acid is introduced into the receiver 15 in the initial stage of distillation and thereafter acts as a collector agent for ammonia nitrogen.

After the ammonia nitrogen has been distilled off from the distillation still 4, steam distillation is continued for a short period. When the amount of liquid in the fraction collector 14 reaches a predetermined quantity by addition of condensed water, the movable receiver 15 descends, and a liquid distillate is collected in the fraction receiver 7. At this time, the microswitch 18 is simultaneously turned on, and a starting signal is sent to the timer 11. Thus, the changeover valves 3a and 3b are switched over to the passages represented by the dotted lines, and distillation liquid residue is discharged. The two-way valve 26 is switched over to the passage represented by the dotted line to introduce a predetermined quantity of washing water to the fraction collector 14 by means of a carrier gas. The empty movable receiver 15, after washing with water, returns to the position shown in the drawing.

In accordance with the signal of the timer which is intercoupled with the movement of the receiver 15 or is started at the corresponding point of time $t_1 + \Delta t$, the motor 10d is driven, and the stand 19 is moved so that the succeeding fraction receiver 7 comes under the movable receiver 15. In accordance with the signal from the timer at a point of time $t_2 (= t_1 + 1 - 2$ minutes, for example) when the period of time required for discharging distillation liquid residue has elapsed, the changeover valves in the addition means 20a, 20b and 20c are switched over to the passages represented by the dotted lines (which can also be actuated at the point of time $t_1$); the selector valves 2a and 2b are switched over to the next passages; and the changeover valves 26, 3a and 3b are switched over to the passages represented by the solid lines, respectively. Thus, the succeeding cycle is started. In order to prevent unnecessary steam from accumulating in the system, a solenoid valve which is operated by the timer to open at a point of time "0" (or $t_2$) and close at $t_1$ may be installed in the branch pipe r of the pipe $a_1$.

As is clear from the above description, the numeral "18 [$t_1$]" in FIG. 7 indicates that the microswitch 18 sends the starting signal to the timer at a time $t_1$. In FIG. 7, 2 ($t_2$) and the like indicate that the passages of the selector valves in the apparatus 2 are switched over all at once at a time $t_2$ in one cycle, and 3 ($t_1$ or $t_1 + \Delta t$, $t_2$) indicates that the changeover valves in the apparatus 3 are switched all at once to the passages represented by the dotted lines at a time $t_1$ or $t_1 + \Delta t$, and switched back to the passages represented by the solid lines at a time $t_2$, respectively.

As described above in detail, one of the major problems in the automation of an analysis process has been solved by the present invention which has succeeded in providing a successive automation process including a distillation process for preparing samples for analysis. It is to be noted that the present invention affords reduction of labor in chemical process analysis and the like.

While the invention has been particularly shown and described with reference to preferred embodiments thereof, it will be understood by those skilled in the art that the foregoing and other changes and modifications can be made without departing from the spirit and scope of the present invention.

I claim:

1. An apparatus for automatically preparing samples for analysis which comprises inert gas charging means, multi-way selector liquid sampler means operated by a timer, liquid sampler charging and discharging means operated by the timer, a distillation still, fraction selector means and fraction receivers, which are connected in that order by pipe lines, said liquid sample charging and discharging means including a multi-way changeover valve, said liquid sample charging and discharging means forming a passage extending from said multi-way selector liquid sampler means through the multi-way changeover valve to the bottom of said distillation still for introduction of a liquid sample into said distillation still, said liquid sample charging and discharging means forming a passage connecting said multi-way selector liquid sampler means, said multi-way changeover valve and space in said distillation still and a passage connecting the bottom of said distillation still, said multi-way changeover valve, and outside of the system for discharging of a distillation liquid residue outside of the system, whereby specific fractions of a plurality of liquid samples can be automatically and successively collected by distillation.

2. The apparatus as set forth in claim 1 in which the multi-way selector liquid sampler means comprises a pair of multi-way slide selector valves, and plural starting sample containers which are connected to and placed between the multi-way slide selector valves.

3. The apparatus as set forth in claim 1 in which the fraction selector means is a multi-way slide selector valve.

4. The apparatus as set forth in claim 1 in which the fraction selector means is a gravimetric fraction collector comprising a movable receiver having an outlet at the bottom thereof and a fixed stopper ground fitted to said bottom, and said movable receiver is connected mechanically to a microswitch via a fulcrum, said microswitch operating to impart a starting signal to said timer.

5. The apparatus as set forth in claim 1 in which a condenser is interposed between the distillation still and the fraction selector means.

6. The apparatus as set forth in claim 1 in which a reagent addition means is interposed in front of the multi-way selector liquid sampler means, the liquid sample charging and discharging means or the fraction selector means, said reagent addition means comprising a pair of four-way changeover valves, a pair of metering tubes provided respectively in two lines connecting the valves, and a reagent container and an overflow-preventing tube, respectively connected to each of the four way changeover valves.

7. The apparatus as set forth in claim 1 in which a plurality of fraction receivers are placed on a stand which is moved by a driving motor operated by said timer.

8. Apparatus for automatically preparing samples for analysis of a diacetyl-odor component, which comprises, inert gas charging means, multi-way selector liquid sampler means operated by a timer, liquid sample charging and discharging means operated by the timer, a gas washer, a condenser, diacetyl-odor collecter agent addition means, fraction selector means, and fraction receivers, which are connected in that order by pipe lines, said liquid sample charging and discharging means including a multi-way changeover valve; said liquid sample charging and discharging means forming a passage connecting said multi-way selector liquid sampler means, multiway changeover valve, and the bottom of said gas washer for introduction of a liquid sample into said gas washer and subsequent-washing thereof with gas, said liquid sample charging and discharging means forming a passage connecting said multi-way selector liquid sampler means, multi-way changeover valve, and space in said gas washer and a passage connecting the bottom of said gas washer, multi-way changeover valve, and outside of the system for discharging a gas-washed liquid residue outside of the system from said gas washer, whereby a plurality of samples for analysis containing a diacetyl-odor component in a concentrated state can be automatically and successively collected from the corresponding starting samples containing a diacetyl-odor component.

9. Apparatus for automatically and successively preparing samples for the Kjeldahl titration method from samples containing ammonia nitrogen, which comprises gas charging means, aqueous sodium hydroxide solution addition means, multi-way selector liquid sampler means operated by a timer, liquid sample charging and discharging means operated by the timer, a distillation still, a condenser, aqueous sulfuric acid solution addition means, fraction selector means, and fraction receivers, which are connected in that order by pipe lines, and which further comprises a branch pipe line extending from the outlet of said gas charging means to said fraction selector means and including washing water addition means operated by the timer, a steam generator being connected via a branch pipe line to the pipe line connecting said gas charging means and said aqueous sodium hydroxide solution addition means, said sample charging and discharging means containing a multi-way changeover valve, said sample charging and discharging means forming a passage connecting said multi-way selector sampler means, the multi-way changeover valve, and the bottom of the distillation still for charging of a liquid sample to said distillation still and carrying out of a subsequent distillation operation, said sample charging and discharging means forming a passage connecting said multi-way selector liquid sampler means, the multi-way changeover valve, and space in said distillation still and a passage connecting the bottom of said distillation still, the multi-way changeover valve, and outside of the system for discharging of a distillation liquid residue from said distillation still outside of the system.

10. In the preparation of corresponding samples for analysis containing a diacetyl-odor component in a concentrated state from a plurality of aqueous solution samples containing diacetyl-odor components, the improvement which comprises washing said aqueous solution samples in a gas washer with an inert gas at a temperature higher than the boiling point of diacetyl and lower than the boiling point of water, cooling the diacetyl-odor component accompanied by said inert gas, thereafter collecting the component in collector means by using a collector agent for converting the diacetyl-odor component to diacetyl dioxime, and employing said inert gas as a carrier gas for charging said aqueous solution samples into said gas washer and for discharging a gas-washed sample residue from said gas washer and as a carrier gas for charging said collector agent into said collector means.

* * * * *